(12) United States Patent
Jacobs et al.

(10) Patent No.: US 6,282,359 B1
(45) Date of Patent: Aug. 28, 2001

(54) INJECTION MOLDED LIGHT PIPE

(75) Inventors: Adam Jacobs, Glen Ridge, NJ (US);
Tomasz Momot, Ossining, NY (US)

(73) Assignee: Electro Optical Sciences Inc.,
Irvington, NY (US)

( * ) Notice: Subject to any disclaimer, the term of this patent is extended or adjusted under 35 U.S.C. 154(b) by 0 days.

(21) Appl. No.: 09/467,344

(22) Filed: Dec. 20, 1999

Related U.S. Application Data

(60) Provisional application No. 60/167,711, filed on Nov. 27, 1999.

(51) Int. Cl.$^7$ ...................................................... G02B 6/00
(52) U.S. Cl. ......................... 385/133; 385/147; 385/901; 382/100
(58) Field of Search ...................................... 385/133, 147, 385/901, 141–145, 12, 123; 382/100; 433/29

(56) References Cited

U.S. PATENT DOCUMENTS 5,960,147 * 9/1999 Muramatsu et al. ............. 385/147 X
6,201,880 * 3/2001 Elbaum et al. ....................... 382/100

* cited by examiner

Primary Examiner—Phan T. H. Palmer
(74) Attorney, Agent, or Firm—Rodney T Hodgson

(57) ABSTRACT

An injection molded light pipe having a sharp curve is proposed, wherein the injection molding mark is on the inside surface of the sharp curve. The light pipe has a 180° curve with a radius of curvature less than approximately 3 times the diameter of the light pipe.

10 Claims, 4 Drawing Sheets

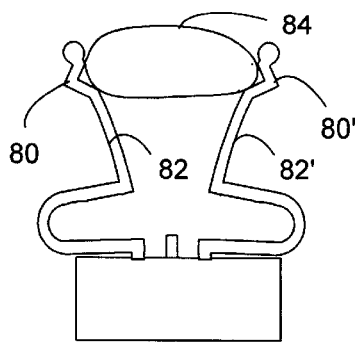
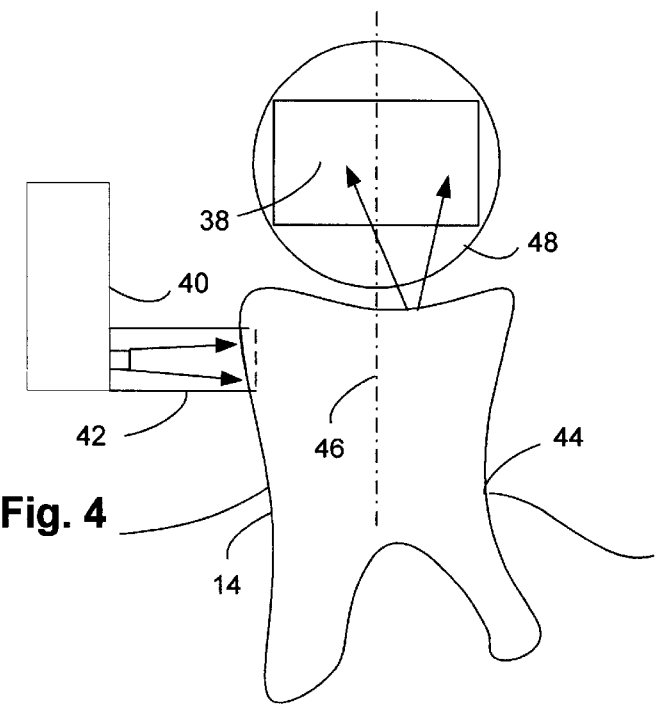
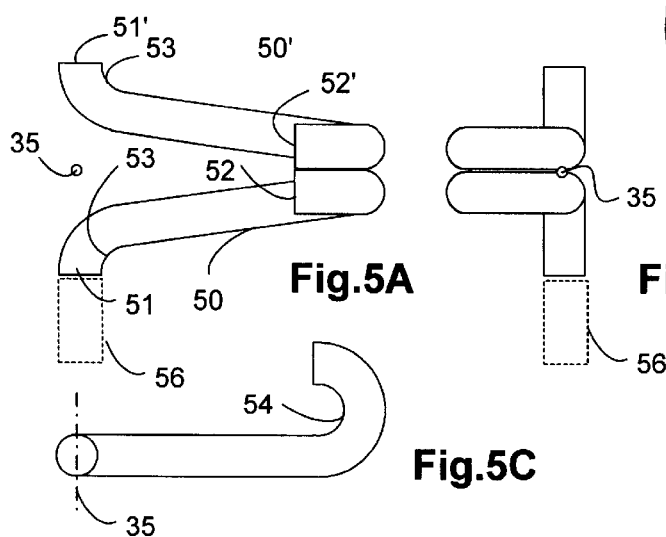
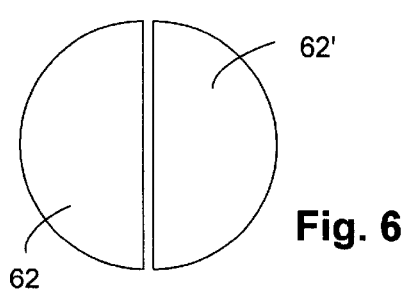
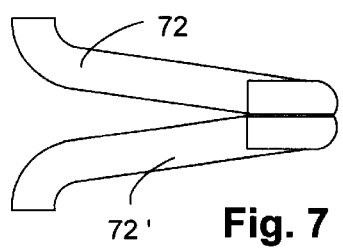

INJECTION MOLDED LIGHT PIPE

CROSS REFERENCE TO RELATED APPLICATIONS

This application is related to a copending U.S. application Ser. No. 08/778,001 filed Dec. 31, 1916 (now U.S. Pat. No. 6,201,880), which is incorporated herein by reference in its entirety including incorporated material. This application is related to an application by the same inventors deposited on the same day as the present application entitled "Apparatus for holding optical instruments in a reproducible position with respect to teeth". This application claims priority pursuant to 35 U.S.C. 119(e) to U.S. Provisional Applications: Application No. 60/167711 filed Nov. 27, 1999 which is incorporated herein by reference in its entirety including incorporated material.

FIELD OF THE INVENTION

The field of the invention is the field of imaging of teeth in a mouth.

BACKGROUND OF THE INVENTION

The above identified U.S. patent application summarizes the background of the art of imaging of teeth in great detail. In brief, the prior art to the above identified application is deficient in that images of teeth taken with light transillumination were not reproducible. The above identified application teaches that the illumination source and imaging system must be held in a reproducible and repeatable position with respect to the tooth by anchoring the source and imaging system physically with respect to the tooth. The above identified application teaches that the light for illumination may be piped around in tight confines in a mouth using a light pipe material.

SUMMARY OF THE INVENTION

The present invention is a light pipe apparatus which has little loss even while incorporating sharp bends. The light pipe is injection molded using a suitable substance which is transparent when solidified. The injection mold point is at the inside of a curve of the light pipe. The invention has a light pipe apparatus with a light pipe with a sharp 180° bend for taking light from a handpiece, moving the light to a position to direct light from the end of the light pipe back towards and optical imaging system in the handpiece so that the light impinges on a tooth placed between the end of the lightpipe and the imaging system of the handpiece.

BRIEF DESCRIPTION OF THE DRAWINGS

FIG. 4 is a drawing of an alternative embodiment of the invention

FIGS. 5A–5C are the drawings of an embodiment of the invention.

FIG. 6 is a drawing of an embodiment of the invention.

FIG. 7 is a drawing of an embodiment of the invention.

FIG. 8 is a drawing of an embodiment of the invention.

DETAILED DESCRIPTION OF THE INVENTION

Figure 1A:
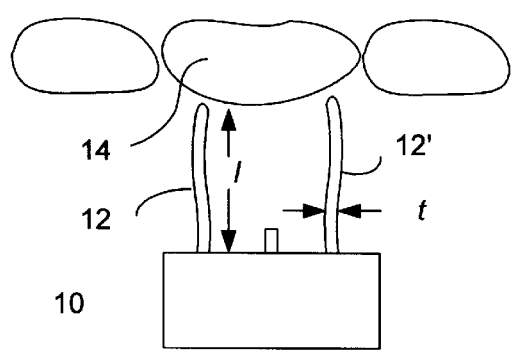
FIGS. 1A and 1B show the spring prongs of the invention removed from and in place against proximal surfaces of a tooth.
Figure 1B:
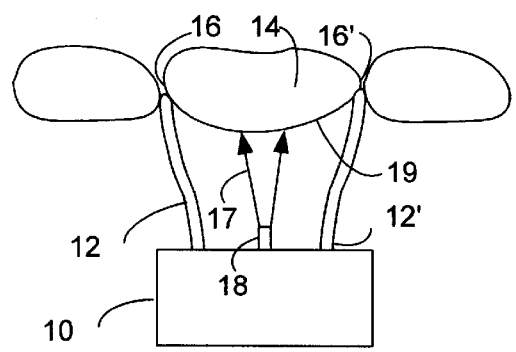

FIG. 1A shows a sketch of a body 10 having two prongs 12 and 12' attached. The prongs are near but do not touch a tooth 14 in a row of teeth. FIGS. 1A and 1B are shown looking at the top of the teeth in a bottom row of teeth as an example. As the body 10 moves towards the tooth 14 so that the ends of the prongs 12 and 12' touch the tooth 14, the prongs 12 and 12' elastically separate at the distal ends and contact the proximal surfaces of the tooth 14 at positions 16 and 16'. The body 10 is then held in a repeatable position with respect to tooth 14 so that a source of illumination 18 connected to body 10 may radiate light rays 17 on to the surface 19. The source of illumination 18 may be a light pipe, a laser, or a light emitting diode (LED), or other light source as known in the art. Prongs 12 and 12' are preferably long thin plates having thickness t, length l, and height h (not shown) in order that the prongs 12 may act as springs to hold teeth of different dimensions in a reproducible way.

Figure 2A:
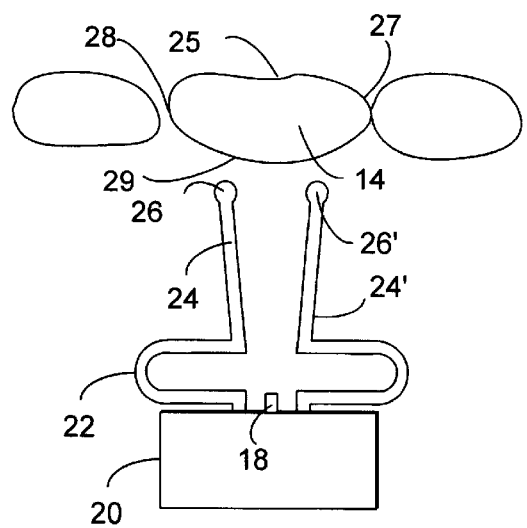
FIGS. 2A and 2B show the most preferred spring prongs of the invention removed from and in place against proximal surfaces of a tooth.
Figure 2B:
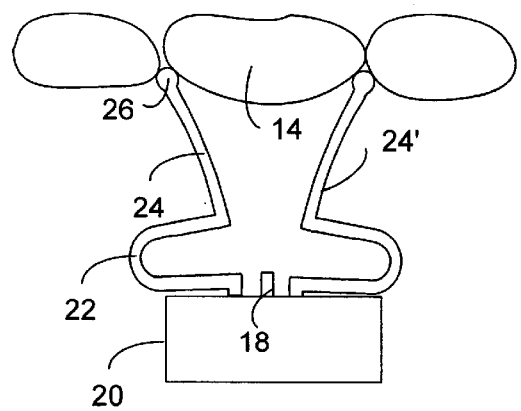

FIGS. 2A and 2B show the prongs of the most preferable embodiment of the invention. A U shaped plate 22 is joined to the body 20 at one end, and prongs 24 are joined to the U shaped plate 22 at the other end. When the prongs 24 and 24' are brought into contact with and pressed against tooth 14, the prongs 24 and 24' separate until the distal ends of the prongs lodge in the V shaped space between the tooth 14 and the neighboring teeth. Prongs 24 and 24' are shown having cylindrically shaped ends 26 and 26' for this purpose. Proximal surfaces (next to the neighboring teeth) 27 and 28 and labial or buccal surfaces 25 and 29 of tooth 14 are shown. The U shaped plate allows for a greater spring displacement while holding the illumination source 18 near the tooth 14. It is important the prongs open at a slight angle as noted in FIG. 2a so that there is a moment arm about the pivot points at the ends of the U to open the prongs when the prongs are pushed against the tooth. As the end of the prong slides against the tooth towards the proximal surface, another moment arm opens the U to give a large displacement of the distal end of the prong.

Figure 3A:
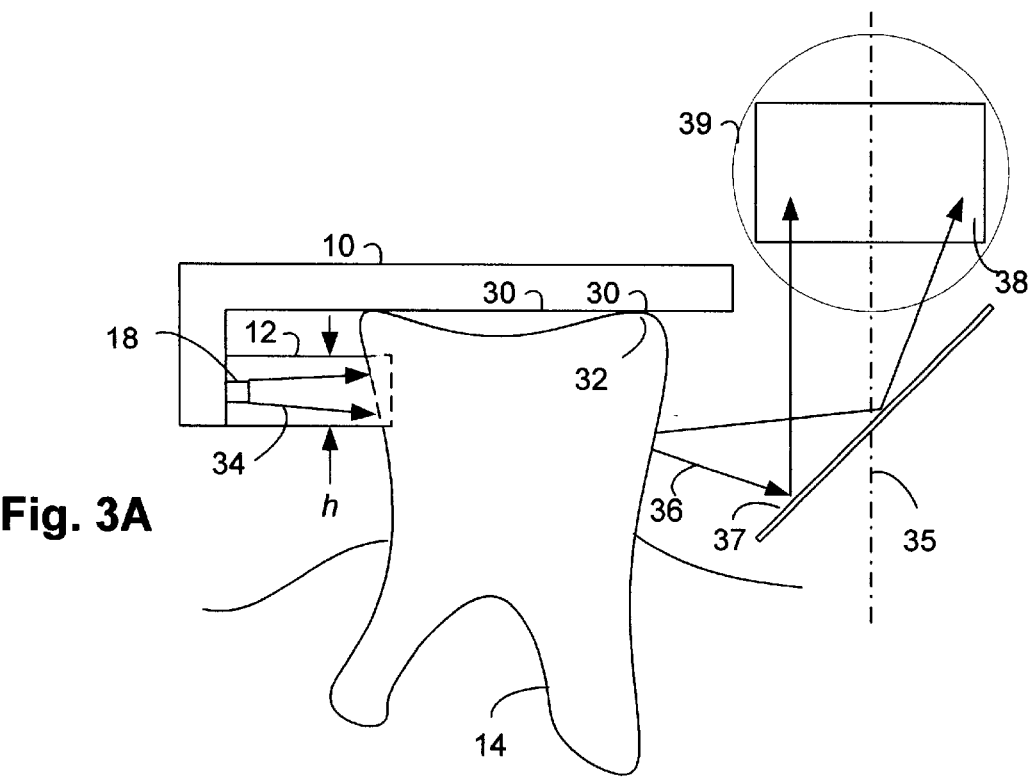
FIG. 3A and 3B show side views of the spring prongs of the invention in place against a proximal surface of a tooth when the most preferred embodiment of the invention is rotated.
Figure 3B:
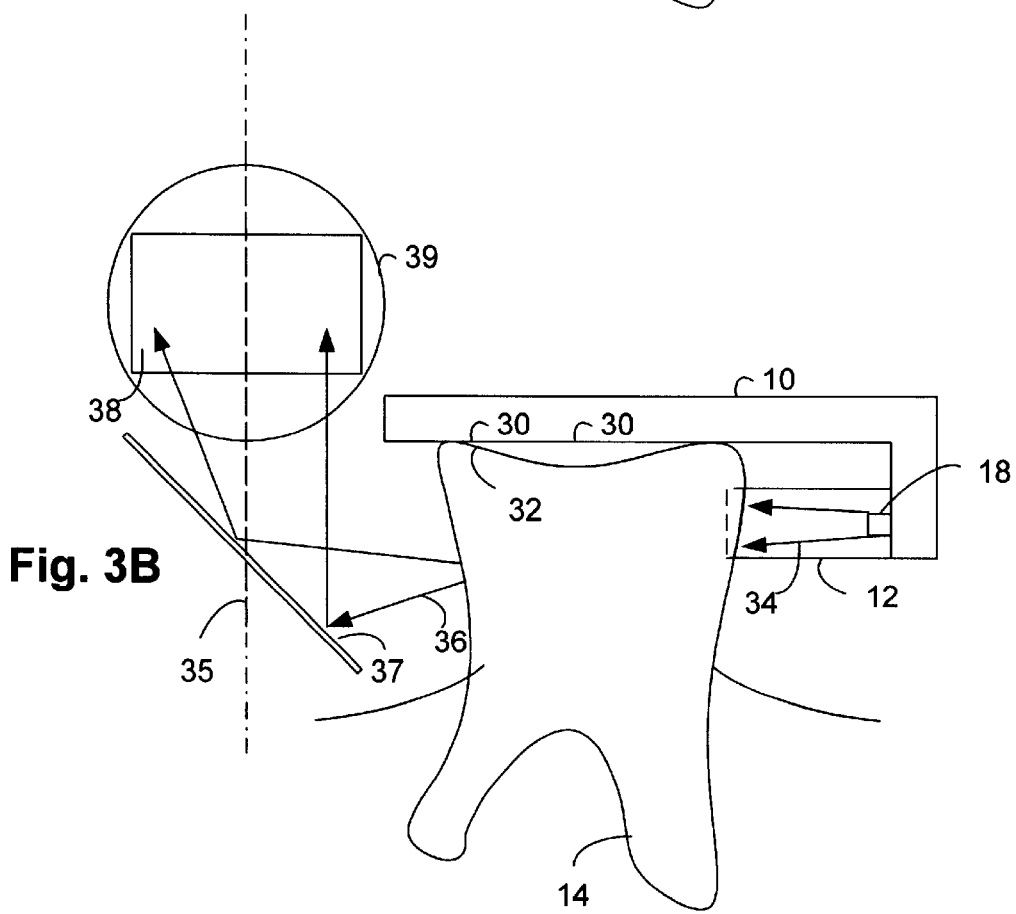

FIGS. 3A and 3B show a side view of the tooth 14 with prongs 12 holding illumination source 18 in place. Body 10 is shown having a surface 30 resting on the occlusal surface 32 of tooth 14. The combination of prongs 12 contacting the proximal surfaces of tooth 14 and the body 10 touching surface 32 of the tooth holds the illumination source 18 for repeatable imaging of the tooth. Light rays 34 are shown incident on the tooth 14, and light rays 36 which have been transmitted by the tooth 14 are shown exiting from the opposite face of the tooth to impinge on mirror 37. Mirror 37 is held fixed with respect to body 10. Light rays 36 are shown reflected from mirror 37 to mirror 38, which is fixed with respect to a handle 39. Light rays 36 are reflected from mirror 39 to an imaging system (not shown) which produces an electronic image of tooth 14 using transilluminated light through the tooth 14. Body 10 is rotatably connected to handle 39 so that rotating body 10 around an axis 35 fixed with respect to handle 39 allows imaging of both the labial (FIG. 3A) and buccal (FIG. 3B) surfaces of tooth 14.

FIG. 4 shows an alternative embodiment of the invention, where the occlusal surface 41 of the tooth 14 is imaged through handle 48 while the body 40 is held in a reproducible position with respect to tooth 14 by means of spring prongs 42. The prongs 42 may be held in the V shaped grooves between tooth 14 and neighboring teeth in a reproducible position with respect to the gum line 44.

In the all the forgoing embodiments, the body 40 may or may not rest on a surface of the tooth as long as the prongs hold the body in a reproducible position with respect to the tooth. For some applications, the reproducibility of the angle of illumination and imaging is sufficient to obtain reproducible images with just the prongs contacting the proximal tooth surfaces. For instance, the operator may hold the body so that the prongs contact the proximal surfaces of the teeth and also the gum line. The inventors have found that image quality is much enhanced if the tooth is illuminated low on the tooth towards the gum line. In adults, the best results are obtained if the tooth is illuminated 4 to 7 mm from the incisal or occlusal surface, and more particularly 5–6 mm, while in children the best results occur for illumination 4 to 5 mm from the incisal or occlusal surface of the tooth.

If a portion of the body is in contact with the occlusal surface 41 of the tooth 14 in FIG. 4, at least a portion of the body must be transparent or shaped to allow light to propagate from the tooth through the body to the imaging system. Note that rotating (not shown) body 40 about axis 46 allows imaging of the same occlusal surface, but with illumination from different sides of the tooth.

Handles 39 and 48 are typically hollow tubes shaped for conducting light from a mirror 38 to an imaging system contained in a handpiece (not shown) which connects removably to the handle 39 or 48. FIGS. 3 and 4 are drawn looking from the handpiece down the handle at a mirror 48 or 38 fixed with respect to the handle. Light is also conducted from the handpiece to the body for illumination in the most preferred embodiment. A light pipe (position shown later) in the handpiece is in close proximity to a light pipe connected to the body.

FIGS. 5A–C show plan, side and end elevation views of an innovative solution to the problem of moving light around in the tight confines of a mouth. Light is brought from the handpiece by a lightpipe in position shown by the dotted outline 56 into light pipe 50 through face 51 and exits through face 52. Lightpipe 50 is connected to the body 10. The lightpipe 50 perferably is round with a cross sectional area A, but it may have a square, rectangular, oval, or other cross section as is known in the art. The light pipe has a length l measured along the curving axis. The light pipe is long enough that $l^2>>>A$. The light pipe 50 is bent approximately 90° at position 53, and approximately 180° at position 54, so that light is piped around and sent back towards the handle 39. This innovative light pipe ensures that the light source and the imaging system for the transillumination may both be contained in the same handle which is introduced into the mouth.

Rotation of lightpipe 50 and 50' about axis 35 brings lightpipe 50' in position to receive light when the body 10 rotates 180° about the handle 39.

In order that light pipes 50 and 50' may be made inexpensively, they should be made by injection molding of a suitable polymer material. It is important that the injection mold mark be placed in a position to minimize light loss in a light pipe which has such tight turns, where the radius of curvature R of the light pipe is less than $10 A^{1/2}$. Such positioning is even more important when the radius of curvature R of the light pipe is less than $3 A^{1/2}$ The inventors have found that injection molding where the injection takes place on an inside curve of the light pipe such as at position 53 and 54 noted on FIG. 5A and 5C produces a light pipe which scatters less light, and that such injection molded light pipes are the most preferable light pipes for the invention. The inventors have found that acrylic light pipes, where the index of refraction of the acrylic is 1.49, may support a 180° curve of radius of curvature 3 mm for a light pipe 1.6 mm in diameter.

FIG. 6 shows that the light pipe end faces 62 and 62' may be formed in the shape of a D, so that the spots of light from the two light pipes may be closer to the center of the tooth. Light pipes 72 and 72' are shown with such end faces in FIG. 7.

FIG. 8 shows a modification of the prongs of the invention in case a single tooth is to be imaged. Detents 80 and 80' in the prongs 82 and 82' grasp the tooth 84 on proximal surfaces.

Figure 9:
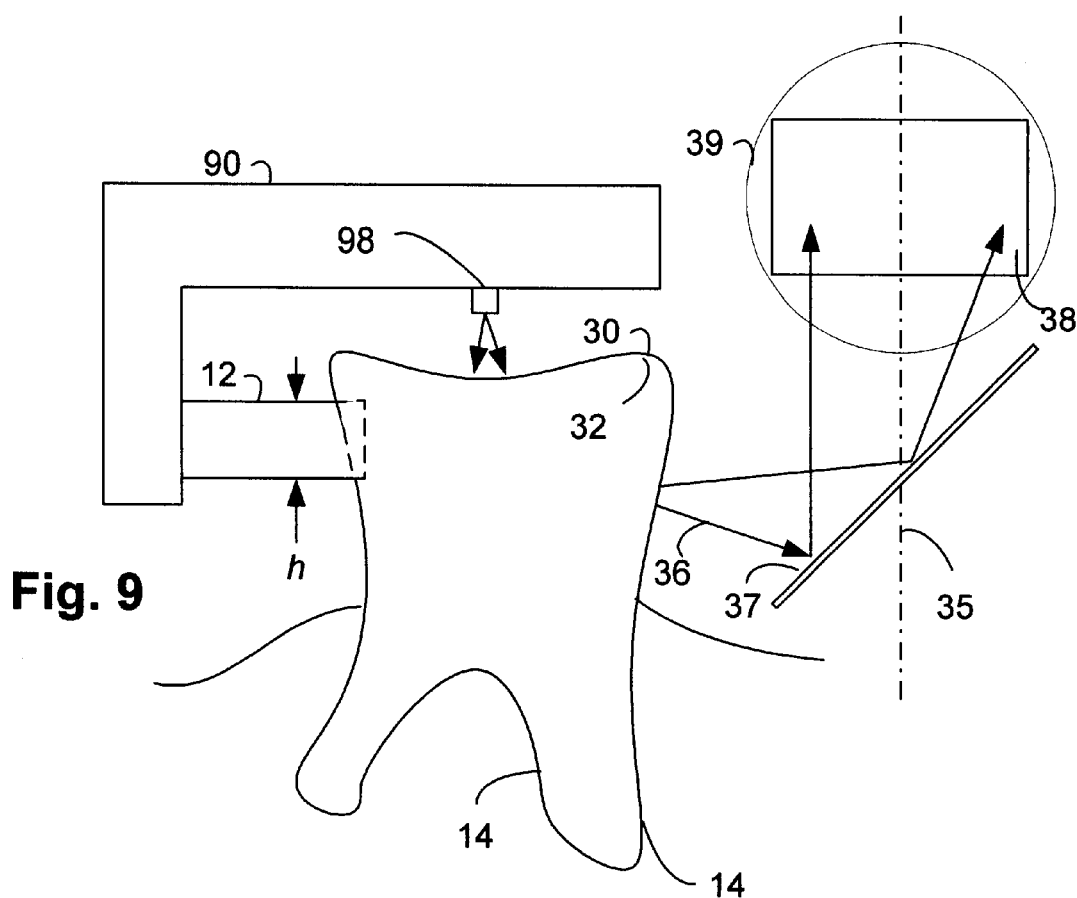
FIG. 9 is a drawing of an embodiment of the invention.

FIG. 9 shows a sketch of an embodiment of the invention where the illumination source 98 illuminates the occlusal surface of the tooth 14 while the tooth 14 is held by prongs on the labial or buccal side, and the other labial or buccal side is imaged by the imaging system.

Figure 10:
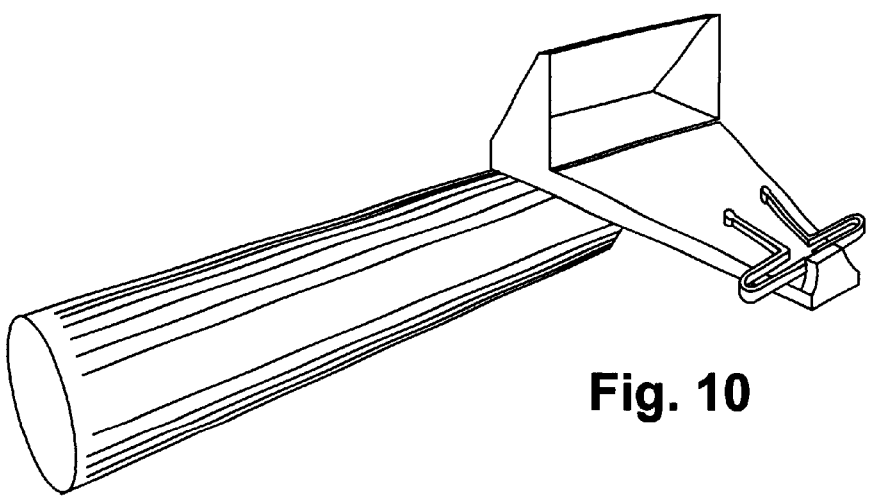
FIG. 10 is a drawing of a disposable mouthpiece of the invention.

FIG. 10 shows a perspective sketch of the handle and the rotatable body of the present invention.

Obviously, many modifications and variations of the present invention are possible in light of the above teachings. It is therefore to be understood that, within the scope of the appended claims, the invention may be practiced otherwise than as specifically described.

We claim:

1. A light pipe, comprising:
an extended transparent body having a substantially constant cross sectional area A along an axis of length l, where $l^2>>>A$, and wherein the axis has approximately 180° first curve with a radius $R<10A^{1/2}$, and wherein the body has a flat first end face approximately perpendicular to the axis for introducing light into the body, and a flat second end face approximately perpendicular to the axis for the light to exit the body and shine light back in the direction of the first end face.

2. The light pipe of claim 1, wherein the second end face is in the shape of a D.

3. The light pipe of claim 1, wherein the extended body has a second approximately 90° curve near the first end face, and wherein the first and second curves are in approximately perpendicular directions.

4. The light pipe of claim 3, wherein the second end face is in the shape of a D.

5. The light pipe of claim 4, wherein a second light pipe with a shape substantially a mirror image of the first light pipe is mounted with the two D faces in close proximity so that light piped through both light pipes irradiates a surface in two spots of close proximity.

6. The light pipe of claim 1, wherein the body is produced by injection molding, and wherein an injection molding mark is on the surface of the body at the inside of the curve.

7. The light pipe of claim 6, wherein the extended body has a first end and a second end with end faces substantially perpendicular to the axis, and wherein the first end face is in the shape of a D.

8. The light pipe of claim 6, wherein the extended body has a first end and a second end with end faces substantially perpendicular to the axis, and wherein the body has a first U shaped curve through approximately 180° at the first end and a second approximately 90° curve at the second end, and wherein the first and second curves are in approximately perpendicular directions.

9. The light pipe of claim 8, wherein the first end face is in the shape of a D.

10. The light pipe of claim 9, wherein a second light pipe with a shape substantially a mirror image of the first light pipe is mounted with the two D faces in close proximity so that light piped through both light pipes irradiates a surface in two spots of close proximity.

\* \* \* \* \*